(12) United States Patent
Yunoki et al.

(10) Patent No.: US 7,378,367 B2
(45) Date of Patent: May 27, 2008

(54) CATALYST FOR PRODUCTION OF ACRYLIC ACID AND PROCESS FOR PRODUCTION OF ACRYLIC ACID USING THE CATALYST

(75) Inventors: Hiromi Yunoki, Himeji (JP); Michio Tanimoto, Himeji (JP)

(73) Assignee: Nippon Shokubai Co., Ltd., Osaka (JP)

(*) Notice: Subject to any disclaimer, the term of this patent is extended or adjusted under 35 U.S.C. 154(b) by 277 days.

(21) Appl. No.: 11/078,680

(22) Filed: Mar. 11, 2005

(65) Prior Publication Data

US 2005/0215818 A1    Sep. 29, 2005

(30) Foreign Application Priority Data

| | | |
|---|---|---|
| Mar. 25, 2004 | (JP) | ................. 2004-089948 |
| May 14, 2004 | (JP) | ................. 2004-145313 |
| Jun. 2, 2004 | (JP) | ................. 2004-164969 |
| Jun. 4, 2004 | (JP) | ................. 2004-167464 |

(51) Int. Cl.
*B01J 23/00* (2006.01)
*C07C 51/235* (2006.01)

(52) U.S. Cl. .................... 502/312; 562/535
(58) Field of Classification Search ............. 502/312; 562/535

See application file for complete search history.

(56) References Cited

U.S. PATENT DOCUMENTS

| | | |
|---|---|---|
| 4,025,549 A | 5/1977 | Ferlazzo et al. |
| 4,289,654 A | 9/1981 | Bertolini et al. |
| 5,153,162 A | 10/1992 | Kurimoto et al. |
| 5,446,004 A | 8/1995 | Tenten et al. |
| 5,493,052 A | 2/1996 | Tenten et al. |
| 5,677,261 A | 10/1997 | Tenten et al. |
| 5,910,608 A | 6/1999 | Tenten et al. |
| 5,959,143 A | 9/1999 | Sugi et al. |
| 6,084,126 A | 7/2000 | Hibst et al. |
| 6,762,148 B2 | 7/2004 | Ohishi et al. |

FOREIGN PATENT DOCUMENTS

| | | |
|---|---|---|
| DE | 197 36 105 A1 | 2/1999 |
| EP | 1 374 992 A1 | 1/2004 |
| JP | 5-96183 A | 4/1993 |
| JP | 6-279030 A | 10/1994 |
| JP | 8-10621 A | 1/1996 |
| JP | 8-252464 A | 10/1996 |
| JP | 8-299797 A | 11/1996 |
| JP | 2001-79408 A | 3/2001 |

*Primary Examiner*—Paul A Zucker

(57) ABSTRACT

A catalyst for production of acrylic acid which catalyst is so high in activity as to give a still higher selectivity of acrylic acid or a long-catalytic-life-time catalyst for production of acrylic acid which catalyst is so high in activity as to be able to give a high acrylic acid yield while suppressing the temperature rise of the oxidation reaction to a low one; and processes for production of acrylic acid using these catalysts. The catalyst includes an oxide and/or a composite oxide as an essential catalytic component, wherein the oxide and/or the composite oxide has a metal element composition shown by general formula (1):

$$Mo_a V_b W_c Cu_d O_x \quad (1)$$

(wherein: when a=12, then $1 \leq b \leq 14$, $0 \leq c \leq 12$, $0 \leq d \leq 10$, and $0 < c+d$; and x is a numerical value determined by oxidation states of the elements);

with any of the vanadium, tungsten, and copper being maldistributed in the surface side or core side of the catalyst.

19 Claims, No Drawings

CATALYST FOR PRODUCTION OF ACRYLIC ACID AND PROCESS FOR PRODUCTION OF ACRYLIC ACID USING THE CATALYST

BACKGROUND OF THE INVENTION

A. Technical Field

The present invention relates to a catalyst for production of acrylic acid and a process for production of acrylic acid using this catalyst.

B. Background Art

As to catalysts for efficient production of acrylic acid by catalytic gas phase oxidation of acrolein (catalysts for production of acrylic acid), there is widely used a catalyst comprising molybdenum and vanadium as essential catalytic components, and various proposals have been made about its production processes.

Examples of these production processes include: (a) a process in which a mixed liquid of starting materials is subjected to evaporation to dryness, and then, to the resultant dried material, there are added polyvinyl alcohol, a water-absorbent resin, and water, and then they are kneaded together and then extrusion-molded (e.g. refer to patent document 1 below); (b) a process in which a mixed liquid of starting materials is spray-dried and then calcined at 400° C., and then the resultant calcined material is supported onto a support with water as a binder by use of such as a rotary drum type supporting device (e.g. refer to patent document 2 below); (c) a process in which a mixed liquid of starting materials is dried by any method of evaporation to dryness, spray drying, drum drying, and gas flow drying, and then, to the resultant dried material, there are added propyl alcohol and water to mix them together, and then the resultant mixture is extrusion-molded (e.g. refer to patent document 3 below); (d) a process in which a mixed liquid of starting materials is spray-dried and then calcined at 400° C., and then the resultant calcined material is supported onto a support with a liquid binder comprising water and an organic compound of higher than 100° C. in boiling point or sublimation temperature under normal pressure (e.g. refer to patent document 4 below); and (e) a process in which a mixed liquid of starting materials is dried and then calcined at 250-500° C., and then the resultant calcined material is supported onto a support with such as aqueous glycerol solution as a binder by use of a tumbling granulator (e.g. refer to patent documents 5 and 6 below).

[Patent Document 1] JP-A-096183/1993 (Kokai)

[Patent Document 2] JP-A-279030/1994 (Kokai)

[Patent Document 3] JP-A-010621/1996 (Kokai)

[Patent Document 4] JP-A-252464/1996 (Kokai)

[Patent Document 5] JP-A-299797/1996 (Kokai)

[Patent Document 6] JP-A-079408/2001 (Kokai)

However, still none of the catalysts for production of acrylic acid which catalysts are obtained by the above prior production processes is sufficient for the aim of the selectivity of acrylic acid which is the objective product. Furthermore, still none of these catalysts can be said to be sufficient for the aims that chemical and physical properties (e.g. properties such as specific surface area, pore volume, pore distribution, acidity/basicity, acid strength/basic strength) of the catalysts are stable for a long time and further that the catalysts enable the efficient production of acrylic acid. Therefore, there has been much room for improvement.

SUMMARY OF THE INVENTION

A. Object of the Invention

Thus, an object of the present invention is to provide: a catalyst for production of acrylic acid which catalyst is so high in activity as to give a still higher selectivity of acrylic acid (which is the objective product) or a long-catalytic-lifetime catalyst for production of acrylic acid which catalyst is so high in activity as to be able to give a high acrylic acid yield while suppressing the temperature rise of the oxidation reaction to a low one; and processes for production of acrylic acid using these catalysts.

B. Disclosure of the Invention

The present inventors diligently studied to solve the above problems. In its process, they have found out that the aforementioned problems can be solved all at once by arranging that tungsten and/or copper besides molybdenum and vanadium should be used as essential metal elements constituting the catalyst and further that a specific metal element should be maldistributed in the surface side and/or core side of the catalyst. In detail, they have found out that: first, if it is arranged that the tungsten should be maldistributed in the surface side of the catalyst and/or the copper should be maldistributed in the core side of the catalyst, then the activity of the catalyst is enhanced and the aforementioned properties of the catalyst are stabilized for a long time; secondly, if it is arranged that the vanadium should be maldistributed in the surface side of the catalyst, then the activity of the catalyst is enhanced and the aforementioned properties of the catalyst are stabilized for a long time; thirdly, if it is arranged that the copper should be maldistributed in the surface side of the catalyst and/or the tungsten should be maldistributed in the core side of the catalyst, then the selectivity of acrylic acid which is the objective product becomes still higher; and fourthly, if it is arranged that the vanadium should be maldistributed in the core side of the catalyst, then the selectivity of acrylic acid which is the objective product becomes still higher. That is to say, if the metal element is maldistributed like in the aforementioned first and second arrangements, then there can be obtained a selectivity of acrylic acid which selectivity is equal to or higher than prior ones while the temperature rise of the oxidation reaction is suppressed to a low one, so that, for a long time, the catalytic life time can be kept and a high acrylic acid yield can be given. On the other hand, if the metal element is maldistributed like in the aforementioned third and fourth arrangements, then there can be obtained a still higher selectivity of acrylic acid. Then, they have completed the present invention by confirming these findings.

Accordingly, a first catalyst according to the present invention for production of acrylic acid comprises an oxide and/or a composite oxide as an essential catalytic component, wherein the oxide and/or the composite oxide has a metal element composition shown by the following general formula (1):

$$Mo_a V_b W_c Cu_d O_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1 \leq b \leq 14$, $0 \leq c \leq 12$, $0 \leq d \leq 10$, and $0 < c+d$; and x is a numerical value determined by oxidation states of the elements);

with the catalyst being characterized in that: the tungsten is maldistributed in the surface side of the catalyst; and/or the copper is maldistributed in the core side of the catalyst.

A second catalyst according to the present invention for production of acrylic acid comprises an oxide and/or a composite oxide as an essential catalytic component, wherein the oxide and/or the composite oxide has a metal element composition shown by the following general formula (1):

$$Mo_aV_bW_cCu_dO_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1 \leq b \leq 14$, $0 \leq c \leq 12$, $0 \leq d \leq 10$, and $0<c+d$; and x is a numerical value determined by oxidation states of the elements);
with the catalyst being characterized in that the vanadium is maldistributed in the surface side of the catalyst.

A third catalyst according to the present invention for production of acrylic acid comprises an oxide and/or a composite oxide as an essential catalytic component, wherein the oxide and/or the composite oxide has a metal element composition shown by the following general formula (1):

$$Mo_aV_bW_cCu_dO_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1 \leq b \leq 14$, $0 \leq c \leq 12$, $0 \leq d \leq 10$, and $0<c+d$; and x is a numerical value determined by oxidation states of the elements);
with the catalyst being characterized in that: the copper is maldistributed in the surface side of the catalyst; and/or the tungsten is maldistributed in the core side of the catalyst.

A fourth catalyst according to the present invention for production of acrylic acid comprises an oxide and/or a composite oxide as an essential catalytic component, wherein the oxide and/or the composite oxide has a metal element composition shown by the following general formula (1):

$$Mo_aV_bW_cCu_dO_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1 \leq b \leq 14$, $0 \leq c \leq 12$, $0 \leq d \leq 10$, and $0<c+d$; and x is a numerical value determined by oxidation states of the elements);
with the catalyst being characterized in that the vanadium is maldistributed in the core side of the catalyst.

In addition, processes according to the present invention for production of acrylic acid are characterized in that the above catalysts according to the present invention for production of acrylic acid (first, second, third, and fourth catalysts for production of acrylic acid) are used when acrylic acid is produced by catalytic gas phase oxidation of acrolein in the presence of molecular oxygen.

C. Effects of the Invention

The present invention can provide, in a long-time oxidation reaction of acrolein, a catalyst for production of acrylic acid which catalyst gives a still higher selectivity of acrylic acid (which is the objective product) or a long-catalytic-life-time catalyst for production of acrylic acid which catalyst is able to give a high acrylic acid yield while suppressing the temperature rise of the oxidation reaction to a low one. In detail, the first or second catalyst according to the present invention for production of acrylic acid is a long-catalytic-life-time catalyst which is able to give a high acrylic acid yield while suppressing the temperature rise of the oxidation reaction to a low one, and the third or fourth catalyst according to the present invention for production of acrylic acid is a catalyst which gives a still higher selectivity of acrylic acid which is the objective product. In addition, the present invention can provide processes for production of acrylic acid using these catalysts.

These and other objects and advantages of the present invention will be more fully apparent from the following detailed disclosure.

DETAILED DESCRIPTION OF THE INVENTION

Hereinafter, detailed descriptions are given about the catalyst according to the present invention for production of acrylic acid and the process according to the present invention for production of acrylic acid using this catalyst. However, the scope of the present invention is not bound to these descriptions. And other than the following illustrations can also be carried out in the form of appropriate modifications of the following illustrations within the scope not departing from the spirit of the present invention.

Any of the first, second, third, and fourth catalysts according to the present invention for production of acrylic acid (which may hereinafter be referred to generically as "catalyst according to the present invention") is a catalyst comprising an oxide and/or a composite oxide as an essential catalytic component, wherein the oxide and/or the composite oxide has a metal element composition shown by the aforementioned general formula (1). On top of that, as is aforementioned, as to the first catalyst for production of acrylic acid (which may hereinafter be referred to as "first catalyst"), it is important that: the tungsten is maldistributed in the surface side of the aforementioned catalyst (which may hereinafter be referred to simply as "surface side"), and/or the copper is maldistributed in the core side of the aforementioned catalyst (which may hereinafter be referred to simply as "core side"). As to the second catalyst for production of acrylic acid (which may hereinafter be referred to as "second catalyst"), it is important that the vanadium is maldistributed in the surface side of the aforementioned catalyst. As to the third catalyst for production of acrylic acid (which may hereinafter be referred to as "third catalyst"), it is important that: the copper is maldistributed in the surface side of the aforementioned catalyst, and/or the tungsten is maldistributed in the core side of the aforementioned catalyst. As to the fourth catalyst for production of acrylic acid (which may hereinafter be referred to as "fourth catalyst"), it is important that the vanadium is maldistributed in the core side of the aforementioned catalyst. If the metal element is maldistributed like in the first and second catalysts, then there can be obtained a selectivity of acrylic acid which selectivity is equal to or higher than prior ones while the temperature rise of the oxidation reaction is suppressed to a low one, so that, for a long time, the catalytic life time can be kept and a high acrylic acid yield can be given. On the other hand, if the metal element is maldistributed like in the third and fourth catalysts, then there can be obtained a still higher selectivity of acrylic acid (than those given by the aforementioned first and second catalysts). In addition, in the present invention, the above metal element composition may include an optional component (e.g. niobium, chromium, manganese, iron, cobalt, nickel, zinc, bismuth, tin, antimony) besides the metal elements shown in the general formula (1) (Mo, V, W, and Cu).

Hereinafter, as to the catalyst according to the present invention, a metal element maldistributed in the surface side (i.e. tungsten in the case of the first catalyst, vanadium in the case of the second catalyst, and copper in the case of the third catalyst) may be referred to as "metal element ($\alpha$)", and a metal element maldistributed in the core side (i.e. copper in the case of the first catalyst, tungsten in the case of the third catalyst, and vanadium in the case of the fourth catalyst) may be referred to as "metal element ($\beta$)".

The form of the catalyst according to the present invention is not limited. For example, it may be as follows:

1) a catalyst obtained by molding (e.g. extrusion molding) of catalyst materials including the catalytic component, specifically, a catalyst which is a molding that comprises the catalytic component as an essential constitutional material without any support as a constitutional material (this catalyst may hereinafter be referred to as molded catalyst); or 2) a catalyst obtained by supporting of catalyst materials including the catalytic component onto a support, specifically, a catalyst which comprises both the catalytic component and a support as essential constitutional materials wherein the above catalytic component is supported on surfaces of the above support and/or inside it (this catalyst may hereinafter be referred to as supported catalyst).

Above all, examples of the form of the supported catalyst cited as 2) above include:

2-1) what is called eggshell type catalyst such that: the catalytic component is supported on surfaces of the support (surface-supported) (it will do that the catalytic component is supported substantially on surfaces of the support, and a part of the catalytic component may exist inside the support), and there is substantially seen a change of property in shape between the original support and the resultant catalyst (specifically, for example, the particle diameter, after the supporting of the catalytic component, is larger than that of the original support alone); and 2-2) a catalyst such that: such as a porous and inside-supportable support is used as the support, and the catalytic component is supported at least inside the support (for example, only inside the support, or both inside the support and on its surfaces).

Furthermore, examples of the form of the supported catalyst cited as 2-2) above include:

2-2-1) what is called uniform type catalyst such that: the catalytic component is supported only inside the support (inside-supported) (it will do that the catalytic component is supported substantially only inside the support, and a part of the catalytic component may exist on surfaces of the support), and there is seen substantially no change of property in shape between the original support and the resultant catalyst (specifically, for example, the particle diameter, after the supporting of the catalytic component, is the same as that of the original support alone); and 2-2-2) a catalyst such that the above two kinds of forms 2-1) and 2-2-1) are combined together, specifically, a combined type catalyst (catalyst of a type in combination of the uniform type and the eggshell type) such that the catalytic component is supported both inside the support and on its surfaces.

Examples of the shape of the catalyst according to the present invention include any shape of such as spheres (including, besides true spheres, other spheres such as flat spheres (such as formed by squashing spheres flat) (e.g. oval spheres) and substantial spheres), pillars (e.g. cylinders, oval cylinders, prisms), (regular) polyhedrons (e.g. dice), rings, and irregular shapes.

Though not limited, the particle diameter (average outer diameter) of the catalyst according to the present invention is favorably in the range of 1 to 15 mm, more favorably 3 to 10 mm. Incidentally, the "average outer diameter" in the present invention is defined as referring to the average of lengths of the longest and shortest portions of the catalyst in particle diameter. For example, as to a truly spherical catalyst, the diameter and the average outer diameter are the same as each other. However, as to a non-truly-spherical catalyst, the average of the longest and shortest outer diameters is the average outer diameter.

In addition, as to cases where the catalyst according to the present invention is the eggshell type catalyst previously cited as 2-1), it is favorable that the thickness of the catalytic component supported on the support is not less than a definite value in any portion. Specifically, the above thickness is favorably not less than 30 μm, more favorably in the range of 60 μm to 5 mm, still more favorably 100 μm to 3 mm.

The degree of the above maldistribution in the catalyst according to the present invention is as follows. As to the maldistribution of the metal element ($\alpha$) in the surface side (maldistribution of tungsten in the case of the first catalyst, maldistribution of vanadium in the case of the second catalyst, or maldistribution of copper in the case of the third catalyst), it will do if the metal element ($\alpha$) (tungsten (tungsten element) in the case of the first catalyst, vanadium (vanadium element) in the case of the second catalyst, copper (copper element) in the case of the third catalyst) contained in the catalytic component is maldistributed in the surface side in an amount larger than half the total content of the metal element ($\alpha$). On the other hand, as to the maldistribution of the metal element ($\beta$) in the core side (maldistribution of copper in the case of the first catalyst, maldistribution of tungsten in the case of the third catalyst, or maldistribution of vanadium in the case of the fourth catalyst), it will do if the metal element ($\beta$) (copper (copper element) in the case of the first catalyst, tungsten (tungsten element) in the case of the third catalyst, vanadium (vanadium element) in the case of the fourth catalyst) contained in the catalytic component is maldistributed in the core side in an amount larger than half the total content of the metal element ($\beta$). The aforementioned problems can easily be solved by maldistributing the prescribed metal element in the surface side or core side in this way.

In the present invention, that the metal element ($\alpha$) is maldistributed in the surface side is defined as meaning that the metal element ($\alpha$) among the aforementioned various metal elements contained in the catalytic component is maldistributed in the surface side. In detail, it is defined as meaning that the above metal element ($\alpha$) is maldistributed in a surface layer portion of the catalyst for production of acrylic acid and/or in the neighborhood of this portion. In more detail, it is defined as meaning that the above metal element ($\alpha$) is distributed mainly in the above surface layer portion and/or mainly in the neighborhood of this surface layer portion with a distribution range of some degree of broadness in the deeper direction than this surface layer portion. Incidentally, the definition of the maldistribution in the surface side, as hereupon referred to, is similarly applicable to all regardless of the types of the aforementioned various forms of the catalyst (e.g. the eggshell type previously cited as 2-1), the uniform type previously cited as 2-2-1), the combined type previously cited as 2-2-2), and the molded type previously cited as 1)).

In the present invention, that the metal element (β) is maldistributed in the core side is defined as meaning that the metal element (β) among the aforementioned various metal elements contained in the catalytic component is maldistributed in the core side. In detail, it can be defined as follows in accordance with the types of the aforementioned forms of the catalyst.

That is to say, in cases where the catalyst according to the present invention is the eggshell type catalyst previously cited as 2-1), then that the metal element (β) is maldistributed in the core side is defined as meaning that, in the catalyst for production of acrylic acid, the above metal element (β) is maldistributed in a portion, contacting with the surfaces of the support, of the catalytic component supported on the support and/or in the neighborhood of this portion. In more detail, it is defined as meaning that the above metal element (β) is distributed mainly in the above contacting portion and/or mainly in the neighborhood of this contacting portion with a distribution range of some degree of broadness in the depth direction opposite to this contacting portion.

On the other hand, in cases where the catalysts according to the present invention are the uniform type previously cited as 2-2-1), the combined type previously cited as 2-2-2), and the molded type previously cited as 1), then that the metal element (β) is maldistributed in the core side is defined as meaning that the above metal element (β) is maldistributed in a central portion of the catalyst for production of acrylic acid and/or in the neighborhood of this portion. In more detail, it is defined as meaning that the above metal element (β) is distributed mainly in the above central portion and/or mainly in the neighborhood of this central portion with a distribution range of some degree of broadness from this central portion up to its periphery.

As to the catalysts according to the present invention, the maldistribution of the prescribed metal elements (metal element (α) and metal element (β)) (contained in the catalytic component) in the surface side and in the core side can be evaluated by measurement using an EPMA (Electron Probe Micro Analyzer) device in accordance with such methods and standards as shown in (i) to (iii) below. In detail, whether the metal element (α) is maldistributed in the surface side or not (the surface-side maldistribution ratio of the metal element (α)) can be evaluated by (i) and (ii) below. Whether the metal element (β) is maldistributed in the core side or not (the core-side maldistribution ratio of the metal element (β)) can be evaluated by (i) and (iii) below. In (i) to (iii) below, measurement conditions and evaluation methods are described in accordance with the types of the forms of the catalyst. Incidentally, also in the below-mentioned detailed description of Examples of some preferred embodiments, the evaluation of the surface-side maldistribution ratio of the metal element (α) and the evaluation of the core-side maldistribution ratio of the metal element (β) shall be carried out by the below-mentioned methods.

(i) The prescribed metal element (metal element (α) or metal element (β)) is individually examined analytically by the measurement using the EPMA device. Specifically, a section including the central portion of the catalyst is targeted and measured (linear-analytically measured) into the prescribed metal element (metal element (α) or metal element (β)) continuously from a one-side outer surface to the opposite-side outer surface in the central-portion-through direction in the above section. Next, the following drawing figure (graph) is obtained in accordance with the types of the forms of the catalyst.

That is to say, in cases where the catalyst according to the present invention is the eggshell type catalyst previously cited as 2-1), then the range of from the support surface to the above outer surface in the measurement position range of from the above central portion to the above outer surfaces is taken as the position range to be analyzed, and there is obtained a drawing figure (graph) which shows relations between the distance $r^1$ (x-axis) of from the above support surface (x=0) to the above outer surface (x=$r^1$) and the X-ray intensity I (y-axis) being measured correspondingly to the existence amount of the prescribed metal element.

On the other hand, in cases where the catalysts according to the present invention are the uniform type previously cited as 2-2-1), the combined type previously cited as 2-2-2), and the molded type previously cited as 1), then the range of from the above central portion to the above outer surface is taken as the position range to be analyzed, and there is obtained a drawing figure (graph) which shows relations between the distance $r^2$ (x-axis) of from the above central portion (x=0) to the above outer surface (x=$r^2$) and the X-ray intensity I (y-axis) being measured correspondingly to the existence amount of the prescribed metal element.

(ii) The method and standard for evaluation of the maldistribution in the surface side is defined in accordance with the types of the forms of the catalyst.

That is to say, in the case of the eggshell type catalyst previously cited as 2-1), then, as to the metal element (α), the integration value $N^{10}$ of the X-ray intensity I is determined throughout the entire position range, to be analyzed, of from the above support surface (x=0) to the above outer surface (x=$r^1$), and the integration value of the X-ray intensity I in all positions (including the following standard position) on the outer surface side of a position (standard position) of $1/2r^1$ from the above support surface (x=0) toward the above outer surface (x=$r^1$) is denoted by $N^{11}$. Then, the surface-side maldistribution ratio Ma (%) as determined from the following formula (a):

$$Ma(\%) = (N^{11}/N^{10}) \times 100 \tag{a}$$

is favorably more than 50%, more favorably not less than 55%, still more favorably not less than 60%. In addition, in this case, the above standard position is more favorably $3/5r^1$, still more favorably $2/3r^1$. In cases where the above evaluation standard is not satisfied, then there is a possibility that the aforementioned problems cannot easily be solved.

On the other hand, in cases where the catalysts according to the present invention are the uniform type previously cited as 2-2-1), the combined type previously cited as 2-2-2), and the molded type previously cited as 1), then, as to the metal element (α), the integration value $N^{20}$ of the X-ray intensity I is determined throughout the entire position range, to be analyzed, of from the above central portion (x=0) to the above outer surface (x=$r^2$), and the integration value of the X-ray intensity I in all positions (including the following standard position) on the outer surface side of a position (standard position) of $1/2r^2$ from the above central portion (x=0) toward the above outer surface (x=$r^2$) is denoted by $N^{21}$. Then, the surface-side maldistribution ratio Mb (%) as determined from the following formula (b):

$$Mb(\%) = (N^{21}/N^{20}) \times 100 \tag{b}$$

is favorably more than 50%, more favorably not less than 55%, still more favorably not less than 60%. In addition, in this case, the above standard position is more favorably $3/5r^2$, still more favorably $2/3r^2$. In cases where the above evaluation standard is not satisfied, then there is a possibility that the aforementioned problems cannot easily be solved.

(iii) The method and standard for evaluation of the maldistribution in the core side is defined in accordance with the types of the forms of the catalyst.

That is to say, in the case of the eggshell type catalyst previously cited as 2-1), then, as to the metal element (β), the integration value $N^{30}$ of the X-ray intensity I is determined throughout the entire position range, to be analyzed, of from the above support surface (x=0) to the above outer surface (x=$r^1$), and the integration value of the X-ray intensity I in all positions (including the following standard position) on the support surface side of a position (standard position) of $1/2r^1$ from the above support surface (x=0) toward the above outer surface (x=$r^1$) is denoted by $N^{31}$ Then, the core-side maldistribution ratio Mc (%) as determined from the following formula (c):

$$Mc(\%)=(N^{31}/N^{30})\times 100 \quad (c)$$

is favorably more than 50%, more favorably not less than 55%, still more favorably not less than 60%. In addition, in this case, the above standard position is more favorably $2/5r^1$, still more favorably $1/3r^1$. In cases where the above evaluation standard is not satisfied, then there is a possibility that the aforementioned problems cannot easily be solved.

On the other hand, in cases where the catalysts according to the present invention are the uniform type previously cited as 2-2-1), the combined type previously cited as 2-2-2), and the molded type previously cited as 1), then, as to the metal element (β), the integration value $N^{40}$ of the X-ray intensity I is determined throughout the entire position range, to be analyzed, of from the above central portion (x=0) to the above outer surface (x=$r^2$), and the integration value of the X-ray intensity I in all positions (including the following standard position) on the central portion side of a position (standard position) of $1/2r^2$ from the above central portion (x=0) toward the above outer surface (x=$r^2$) is denoted by $N^{41}$. Then, the core-side maldistribution ratio Md (%) as determined from the following formula (d):

$$Md(\%)=(N^{41}/N^{40})\times 100 \quad (d)$$

is favorably more than 50%, more favorably not less than 55%, still more favorably not less than 60%. In addition, in this case, the above standard position is more favorably $2/5r^2$, still more favorably $1/3r^2$. In cases where the above evaluation standard is not satisfied, then there is a possibility that the aforementioned problems cannot easily be solved.

In cases where various measurements and analyses about the catalyst according to the present invention are carried out with the EPMA device in the aforementioned ways, then favorable examples of the shape of the catalyst to be measured include shapes of such as spheres (particularly, such as true spheres and substantially true spheres), pillars (particularly, such as cylinders), and rings (particularly, such as rings whose sections are circular), and more favorable examples thereof include the shapes of spheres (particularly, such as true spheres and substantially true spheres). Incidentally, depending on the shape of the catalyst, there can possibly be cases where it is difficult to examine the distribution of the prescribed metal element in accordance with the method for analysis and evaluation using the EPMA device. However, usually, shapes of commonly known catalysts for production of acrylic acid could all be analyzed and evaluated. In addition, as to catalyst sections to be analyzed with the EPMA device, for example, it is recommended that: the cylinder-shaped catalyst should be analyzed as to a cross section (circular section) crossing the center line of the cylinder at right angles; the sphere-shaped catalyst should be analyzed as to a section passing through the center of the sphere; and the ring-shaped catalyst should be analyzed as to a section as given by sectioning a thickness portion (which makes the ring) by a plane which crosses at right angles a plane made by the ring and passes through the center line of the ring.

In cases where the evaluations according to the methods and standards as shown in the aforementioned (i) to (iii) are carried out with the EPMA device, then the particle diameter (average outer diameter) of the catalyst according to the present invention is favorably in the range of 1 to 15 mm, more favorably 3 to 10 mm. If the particle diameter is within the above range, then it follows that there are seen good correlations between the maldistributed state (specified by the analytic methods using the EPMA device) of the prescribed metal element and its effect.

In addition, as to cases where the catalyst according to the present invention is the eggshell type catalyst (previously cited as 2-1)) in cases where the same evaluations as the above are carried out, it is favorable that the thickness of the catalytic component supported on the support is not less than a definite value in any portion. Specifically, the above thickness is favorably not less than 30 μm, more favorably in the range of 60 μm to 5 mm, still more favorably 100 μm to 3 mm.

The catalyst according to the present invention for production of acrylic acid is generally obtained by a process comprising steps such as: a step in which a mixed liquid (being in a state of an aqueous solution or aqueous slurry) of starting materials of which the essential components include tungsten and/or copper as well as molybdenum and vanadium is dried to thus obtain a dried material; a step in which this dried material is molded with such as a liquid binder; and a step in which the resultant molding is calcined.

The above starting materials for obtaining the oxide and/or the composite oxide (wherein the oxide and/or the composite oxide includes, as essential metal elements, tungsten and/or copper as well as molybdenum and vanadium) are selected from among those which are commonly used for this type of catalysts, such as ammonium salts, nitrates, carbonates, chlorides, sulfates, hydroxides, organic acid salts, and oxides of the metal elements. However, the ammonium salts and the nitrates are favorably used.

The mixed liquid of the starting materials will do if it is prepared by processes being commonly used for production of this type of catalysts. Accordingly, the starting materials are mixed in order into water to thus prepare an aqueous solution or aqueous slurry. However, in cases where at least two aqueous solutions or aqueous slurries have been prepared in accordance with the kinds of the starting materials, then it will do to mix these together in order. As to conditions of the above mixing (e.g. mixing order, temperature, pressure, pH), there is no especial limitation.

The mixed liquid of the starting materials, as obtained in the above way, is dried by various methods to thus form it into a dried material. Examples thereof include: a method in which the drying is carried out by heating; and a method in which the drying is carried out under reduced pressure.

As to the heating method for obtaining the dried material and as to the form of the dried material, for example, a powdery dried material may be obtained with such as spray driers and drum driers, or a blocky or flaky dried material may be obtained by heating under a gas flow with such as box type driers and tunnel type driers.

The resultant dried material is processed, if necessary, by a pulverization step and/or classification step for obtaining a powder of an appropriate particle size and then fed to a subsequent molding step. Incidentally, the above particle size of the powder of the dried material is favorably not larger than 500 μm though not limited.

In the molding step, such as a liquid binder can be used for molding the resultant dried material. Specifically, there can be adopted such as: a process in which the liquid binder is added to the resultant dried material to mix them together and then the resultant mixture is molded; and, in cases where the dried material is supported onto a desired support (the supported catalyst is obtained), a process in which the support is beforehand wetted with the liquid binder and then the dried material is added thereto to thus support it.

Incidentally, in order to obtain the catalyst according to the present invention, there can also be adopted, besides the aforementioned general production processes, another process in which: the mixed liquid of the starting materials is used remaining a liquid without being dried, and this liquid is absorbed into a desired support or coated or attached onto this support, and then they are calcined. Therefore, as the mode of supporting the catalytic component onto the support, there can also be cited another mode in which the mixed liquid itself of the starting materials is supported besides the aforementioned mode in which the dried material is supported.

Though not limited, as the above liquid binder, it is possible to use binders which are commonly used for molding and supporting of this type of catalysts. Specifically, it is possible to use water, and besides, such as organic compounds (e.g. ethylene glycol, glycerol, propionic acid, maleic acid, benzyl alcohol, propyl alcohol, polyvinyl alcohol, phenol), nitric acid, ammonium nitrate, ammonium carbonate, and silica sol. In addition, of these, only one kind may be used alone, or at least two kinds may be used in combinations with each other.

Though not limited, the amount of the above liquid binder being used (added) will do if it is set appropriately for such as: molding and supporting methods being adopted; and properties of the dried material powder.

In cases where the catalyst according to the present invention is obtained, then it is possible to use various substances such as: molding assistants which can enhance the moldability; reinforcements for enhancing the strength of the catalyst; and pore-forming agents for formation of appropriate pores in the catalyst; wherein these various substances are commonly used for the purpose of these effects in the production of catalysts. Examples of these various substances include stearic acid, graphite, starch, cellulose, silica, alumina, glass fibers, silicon carbide, and silicon nitride. Those which do not exercise any bad influence on the catalytic performances (e.g. activity, selectivity of objective product) by cause of their addition are favorable. These various substances can be used, for example, in a way of being added to the above liquid binder and/or the mixed liquid of the starting materials to mix them together. As to these various substances, if their addition amount is an excess, then there are cases where they greatly deteriorate the physical strength of the catalyst. Therefore, these various substances are added favorably in such an amount that the physical strength of the catalyst may not be deteriorated to such an extent that it becomes impossible to use the catalyst practically as an industrial catalyst.

As the aforementioned support, there can be used any inert support of a definite shape. Specific usable examples thereof include supports of definite shapes including such as alumina, silica, silica-alumina, titania, magnesia, steatite, and silicon carbide.

In the case of the supported catalyst, the supporting ratio of the catalyst is determined appropriately with consideration given to such as: conditions of the oxidation reaction; and the activity and strength of the catalyst. However, it is favorably in the range of 10 to 70 mass %, more favorably 15 to 50 mass %. The supporting ratio is defined as a value determined by the calculation method as described in the below-mentioned detailed description of Examples of some preferred embodiments.

As molding methods adoptable in the molding step, it will do to use hitherto publicly known methods and means. Examples of applicable molding methods include extrusion-molding methods (extrusion-molding machines), granulation methods (tumbling granulators, centrifugal flow coating devices), Marumerizer methods, tablet-molding methods, impregnation methods, evaporation-to-dryness methods, and spray methods. It is also possible that these methods are used in combination of appropriate selections.

As methods for appropriately adjusting and controlling the distribution amount and existence amount of the metal element ($\alpha$) and/or metal element ($\beta$) (as a catalytic component) in the catalyst surface side or catalyst core side (catalyst center side) (methods for maldistributing the metal element ($\alpha$) and/or metal element ($\beta$) in the catalyst surface side or catalyst core side (catalyst center side)) in the catalyst according to the present invention, for example, there can be adopted such as (A) a process in which: at least two catalyst materials (e.g. mixed liquids of catalytic components, and/or their dried materials) different in compositional amount about the metal element ($\alpha$) and/or metal element ($\beta$) (as a catalytic component) are beforehand prepared, and then each of them is molded (inclusive of being supported) while the distribution amount of the metal element ($\alpha$) and/or metal element ($\beta$) is controlled so as to make a difference between the catalyst surface side and the catalyst core side and be predetermined existence amounts therein.

As to the above process (A), in detail, for example, catalyst materials X and Y are separately prepared as the above at least two catalyst materials, and then thereto there can be applied such as the following processes 1) to 5): 1) a process in which the catalyst material X is tablet-molded, and then moldings obtained by this tablet-molding are used as nucleuses to further tablet-mold the catalyst material Y (nuclear tablet-molding method); 2) a process in which the catalyst material X is extrusion-molded, and then, as to moldings obtained by this extrusion-molding, the catalyst material Y is tablet-mold (nuclear tablet-molding method); 3) a process in which the catalyst material X is supported onto a support by the evaporation-to-dryness method, and then the catalyst material Y is supported thereonto by the evaporation-to-dryness method; 4) a process in which the catalyst material X is supported onto a support by the evaporation-to-dryness method, and then the catalyst material Y is supported thereonto by the tumbling granulation method; and 5) a process in which the catalyst material X is supported onto a support by the evaporation-to-dryness method, and then the catalyst material Y is supported thereonto by the spray method. Incidentally, in the above processes 1) to 5), heat treatment such as drying or calcination can be carried out between the molding or supporting treatments as carried out at least two times. In addition, in the above processes 1) to 5), the amount of the catalyst material being used during each of the molding or supporting treatments as carried out at least two times is not limited. This amount will do if it is set appropriately so that the aforementioned maldistribution of the prescribed catalytic component can be achieved (in other words, the catalyst according to the present invention can be obtained).

In cases where the calcination of the molding is carried out when the catalyst according to the present invention is obtained, then the calcination temperature is favorably in the range of 350 to 450° C., more favorably 380 to 420° C., and the calcination time is favorably in the range of about 1 to about 10 hours. Before the above calcination, heat treatment may preliminarily be carried out at a temperature lower than the above calcination temperature.

The process according to the present invention for production of acrylic acid is characterized in that the above catalyst according to the present invention for production of acrylic acid is used in a process in which acrylic acid is produced by catalytic gas phase oxidation of acrolein in the presence of molecular oxygen. By using the catalyst according to the present invention, the aforementioned problems can be solved all at once and easily.

As to the process in which acrylic acid is produced by catalytic gas phase oxidation of acrolein, there is no especial limitation except the point of using the catalyst according to the present invention as the catalyst. This process can be carried out by use of such devices, methods, and conditions as are commonly used.

The above acrolein is subjected to the catalytic gas phase oxidation generally in a state of a raw gas containing this acrolein. As such a raw gas, a mixed gas comprising acrolein, oxygen, and an inert gas can be used as a matter of course, and besides, an acrolein-containing mixed gas obtained by direct oxidation of propylene can also be used after air or oxygen and further water vapor and other gases have been added thereto if necessary. By-products (such as acrylic acid, acetic acid, carbon oxide, propane, or unreacted propylene) which are contained in the acrolein-containing mixed gas obtained by direct oxidation of propylene do no harm to the catalyst (being used in the present invention) for production of acrylic acid.

The catalytic gas phase oxidation reaction in the present invention may be carried out by either of a one-pass process and a recycling process. As reactors, there can be used such as fixed-bed reactors, fluidized-bed reactors, and moving-bed reactors.

At the mention about conditions of the above reaction, it is possible to adopt conditions which are commonly used for the production of acrylic acid by the catalytic gas phase oxidation reaction. For example, it will do that a mixed gas, comprising such as acrolein 1 to 15 volume % (favorably 4 to 12 volume %), oxygen 0.5 to 25 volume % (favorably 2 to 20 volume %), water vapor 0 to 30 volume % (favorably 0 to 25 volume %), and an inert gas (e.g. nitrogen) 20 to 80 volume % (favorably 50 to 70 volume %), is caused to contact and thereby react with the above catalyst according to the present invention for production of acrylic acid in the temperature range of 200 to 400° C. (favorably 220 to 380° C.), under a pressure of 0.1 to 1 MPa, and at a space velocity of 300 to 10,000 $hr^{-1}$ (STP) (favorably 500 to 5,000 $hr^{-1}$ (STP)).

DETAILED DESCRIPTION OF THE PREFERRED EMBODIMENTS

Hereinafter, the present invention is more specifically illustrated by the following Examples of some preferred embodiments. However, the present invention is not limited to them in any way. In detail, the present invention is illustrated by supported catalysts (eggshell type catalysts) such that the catalytic component is supported only on surfaces of inert supports. However, the present invention is not limited to this type of catalysts or processes for production of acrylic acid using this type of catalysts. Incidentally, hereinafter, for convenience, the unit "mass part(s)" may be referred to simply as "part(s)", and the unit "liter(s)" may be referred to simply as "L".

Details of various measurement and calculation methods in the below-mentioned Examples and Comparative Examples are shown below.

<Method for Calculation of Supporting Ratio>:

Supporting ratio (mass %) = [(mass of catalyst obtained − mass of support used)/mass of catalyst obtained] × 100 < Conversion of acrolein > : Conversion (mol %) of acrolein = (mols of acrolein reacted/mols of acrolein supplied) × 100 < Yield of acrylic acid > : Yield (mol %) of acrylic acid = (mols of acrylic acid formed/mols of acrolein supplied) × 100

< Selectivity of acrylic acid > :

Selectivity (mol %) of acrylic acid

= (mols of acrylic acid formed/mols of acrolein reacted) × 100

< Sectional linear analysis with EPMA > : Analyzer: produced by Shimadzu Corporation, product name: EPMA – 1610 X-ray beam diameter: 1 μm Acceleration voltage: 15 kV Beam current: 0.1 μA Measurement time: 20 msec Data point: 1024 × 1024

Step width (moving width) of X-ray beam: 5 μm

PREPARATION EXAMPLES (Preparation of Dried Materials):

While 20,000 parts of pure water was heat-mixed, 3,000 parts of ammonium molybdate, 663 parts of ammonium metavanadate, and 268 parts of ammonium paratungstate were dissolved thereinto. Separately, while 2,000 parts of pure water was heat-mixed, 1,026 parts of copper nitrate trihydrate was dissolved thereinto. The resultant two aqueous solutions were mixed together, and then 62 parts of antimony trioxide was further added thereto, thus obtaining a mixed liquid of starting materials. The resultant mixed liquid of starting materials was dried with a drum drier and then pulverized into the size of not larger than 500 μm, thus obtaining a dried material (A).

The compositional ratio of the metal elements except oxygen in the dried material (A) having been obtained in the above way was as follows.

Dried material (A): $Mo_{12}V_{4.0}W_{0.7}Cu_{3.0}Sb_{0.3}$

Dried materials (B) to (G) were obtained in the same way as of the above process for preparation of the dried material (A) except that the amounts of the ammonium metavanadate, ammonium paratungstate, and copper nitrate trihydrate being used were changed. The compositional ratios of the metal elements except oxygen in these dried materials were as follows.

Dried material (B): $Mo_{12}V_{4.0}W_{1.3}Cu_{3.0}Sb_{0.3}$
Dried material (C): $Mo_{12}V_{4.0}W_{0.7}Cu_{2.0}Sb_{0.3}$
Dried material (D): $Mo_{12}V_{4.0}W_{1.3}Cu_{2.0}Sb_{0.3}$
Dried material (E): $Mo_{12}V_{3.5}W_{1.3}Cu_{2.0}Sb_{0.3}$
Dried material (F): $Mo_{12}V_{5.0}W_{1.3}Cu_{2.0}Sb_{0.3}$
Dried material (G): $Mo_{12}V_{5.0}W_{0.7}Cu_{3.0}Sb_{0.3}$

[First Catalyst]:

Example 1-1

(Production of Catalyst):

A silica-alumina support of 5.0 mm in average diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, first the dried material (A) was added and thereby supported onto the support. Subsequently, the dried material (B) was added and thereby supported onto the outside of the dried material (A), thus obtaining a supported structure.

Next, this supported structure was taken out and then calcined at 400° C. under an air atmosphere for 6 hours, thus obtaining a spherical catalyst (1-1). Incidentally, as to the dried materials (A) and (B), their amounts of addition into the tumbling granulator were adjusted so that their respective supporting ratios would be 10 mass % after the calcination.

The resultant catalyst (1-1) was cut off into hemispheres along a plane passing through the center of the catalyst. A cut section of this hemispherical catalyst was analyzed with the EPMA device into tungsten and copper linearly from a one-side outer surface through the central portion to the opposite-side outer surface in the above section. Based on the results of this analysis, as to the tungsten, the surface-side maldistribution ratio Ma (%) was determined from the aforementioned formula (.alpha.) with the standard position defined as $1/2r^1$. Along therewith, as to the copper, the core-side maldistribution ratio Mc (%) was determined from the aforementioned formula (c) with the standard position defined as $1/2r^1$. The resutls are shown in Table 1.

(Oxidation Reaction):

A stainless reaction tube of 25 mm in inner diameter and 800 mm in length as heated with a molten nitrate was packed with 100 mL of the catalyst (1-1). Then, a mixed gas of acrolein 4 volume %, oxygen 4 volume %, water vapor 30 volume %, and nitrogen 62 volume % was introduced into the reaction tube at a space velocity of 2,500 $hr^{-1}$ (STP) to thus carry out an oxidation reaction of acrolein continuously. During this, the reaction temperature was adjusted so that the conversion of acrolein might be maintained in the range of 98 to 99 mol %. The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Comparative Example 1-1

(Production of Catalyst):

A silica-alumina support of 4.5 to 5.0 mm in diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, the dried material (A) was added and thereby supported onto the support. The resultant supported structure was taken out and then calcined at 400° C. under an air atmosphere for 6 hours, thus obtaining a spherical catalyst (c1-1). Incidentally, as to the dried material (A), its amount of addition into the tumbling granulator was adjusted so that its supporting ratio would be 20 mass % after the calcination.

As to the resultant catalyst (c1-1), the surface-side maldistribution ratio Ma (%) of the tungsten and the core-side maldistribution ratio Mc (%) of the copper were determined in the same way as of Example 1-1. The results are shown in Table 1.

(Oxidation Reaction):

An oxidation reaction was carried out in the same way as of Example 1-1 except that the catalyst (1-1) was replaced with the catalyst (c1-1). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Comparative Example 1-2

(Production of Catalyst):

A spherical catalyst (c1-2) was obtained in the same way as of the catalyst production process of Comparative Example 1-1 except that the dried material (A) was replaced with the dried material (B).

As to the resultant catalyst (c1-2), the surface-side maldistribution ratio Ma (%) of the tungsten and the core-side maldistribution ratio Mc (%) of the copper were determined in the same way as of Example 1-1. The results are shown in Table 1.

(Oxidation Reaction):

An oxidation reaction was carried out in the same way as of Example 1-1 except that the catalyst (1-1) was replaced with the catalyst (c1-2). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Comparative Example 1-3

(Production of Catalyst):

A spherical catalyst (c1-3) was obtained in the same way as of the catalyst production process of Comparative Example 1-1 except that the dried material (A) was replaced with a mixed powder having been obtained by uniformly mixing the dried materials (A) and (B) in equal quantities together. Incidentally, as to the dried materials (A) and (B), their amounts of addition into the tumbling granulator were adjusted so that their respective supporting ratios would be 10 mass % after the calcination.

As to the resultant catalyst (c1-3), the surface-side maldistribution ratio Ma (%) of the tungsten and the core-side maldistribution ratio Mc (%) of the copper were determined in the same way as of Example 1-1. The results are shown in Table 1.

(Oxidation Reaction):

An oxidation reaction was carried out in the same way as of Example 1-1 except that the catalyst (1-1) was replaced with the catalyst (c1-3). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Example 1-2

(Production of Catalyst):

A spherical catalyst (1-2) was obtained in the same way as of the catalyst production process of Example 1-1 except that the dried material (B) was replaced with the dried material (C).

As to the resultant catalyst (1-2), the surface-side maldistribution ratio Ma (%) of the tungsten and the core-side maldistribution ratio Mc (%) of the copper were determined in the same way as of Example 1-1. The results are shown in Table 1.

(Oxidation Reaction):

An oxidation reaction was carried out in the same way as of Example 1-1 except that the catalyst (1-1) was replaced with the catalyst (1-2). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Comparative Example 1-4

(Production of Catalyst):

A spherical catalyst (c1-4) was obtained in the same way as of the catalyst production process of Comparative Example 1-1 except that the dried material (A) was replaced with the dried material (C).

As to the resultant catalyst (c1-4), the surface-side maldistribution ratio Ma (%) of the tungsten and the core-side maldistribution ratio Mc (%) of the copper were determined in the same way as of Example 1-1. The results are shown in Table 1.

(Oxidation Reaction):

An oxidation reaction was carried out in the same way as of Example 1-1 except that the catalyst (1-1) was replaced with the catalyst (c1-4). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Referential Example 1-1

(Production of Catalyst):

A spherical catalyst (r1-1) was obtained in the same way as of the catalyst production process of Example 1-1 except that the dried material (B) was replaced with the dried material (A), and that the dried material (A) was replaced with the dried material (C).

As to the resultant catalyst (r1-1), the surface-side maldistribution ratio Ma (%) of the tungsten and the core-side maldistribution ratio Mc (%) of the copper were determined in the same way as of Example 1-1. The results are shown in Table 1.

(Oxidation Reaction):

An oxidation reaction was carried out in the same way as of Example 1-1 except that the catalyst (1-1) was replaced with the catalyst (r1-1). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 2.

Examples 1-3 to 1-5

(Production of Catalysts):

Spherical catalysts (1-3), (1-4), and (1-5) were obtained in the same way as of the catalyst production process of Example 1-1 except that the dried material (B) was replaced with the dried materials (D), (E), and (F) respectively.

As to the resultant catalysts (1-3), (1-4), and (1-5), the surfaceside maldistribution ratio Ma (%) of the tungsten and the core-side maldistribution ratio Mo (%) of the copper were determined in the same way as of Example 1-1. The results are shown in Table 1.

(Oxidation Reactions):

Oxidation reactions were carried out in the same way as of Example 1-1 except that the catalyst (1-1) was replaced with the catalysts (1-3), (1-4), and (1-5) respectively. The reaction temperature and the selectivity of acrylic acid at a passage of 100 hours from the start of each oxidation reaction, and the reaction temperature and the selectivity of acrylic acid at a passage of 2,000 hours from the start of each oxidation reaction, are shown in Table 2.

Examples 1-6 to 1-9

(Production of Catalysts):

Spherical catalysts (1-6), (1-7), (1-8), and (1-9) were obtained in the same way as of the catalyst production process of Example 1-1 except that the dried material (A) was replaced with the dried material (B) or (C) respectively, and that the dried material (B) was replaced with the dried material (E) or (F) respectively (for the specific combinations of the dried materials used, refer to Table 1 or 2).

As to the resultant catalysts (1-6), (1-7), (1-8), and (1-9), the surfaceside maldistribution ratio Ma (%) of the tungsten and the core-side maldistribution ratio Mc (%) of the copper were determined in the same way as of Example 1-1. The results are shown in Table 1.

(Oxidation Reactions):

Oxidation reactions were carried out in the same way as of Example 1-1 except that the catalyst (1-1) was replaced with the catalysts (1-6), (1-7), (1-8), and (1-9) respectively. The reaction temperature and the selectivity of acrylic acid at a passage of 100 hours from the start of each oxidation reaction, and the reaction temperature and the selectivity of acrylic acid at a passage of 2,000 hours from the start of each oxidation reaction, are shown in Table 2.

Example 1-10

(Oxidation Reaction):

A stainless reaction tube of 25 mm in inner diameter and 3,000 mm in length as heated with a molten nitrate was packed with 1,000 mL of the catalyst (1-2). Then, a mixed gas of acrolein 5 volume %, air 25 volume %, water vapor 30 volume %, and an inert gas (e.g. nitrogen) 40 volume % was introduced into the reaction tube at a space velocity of 1,600 hr$^{-1}$ (STP) to thus carry out an oxidation reaction. The results of the oxidation reaction at a passage of 100 hours from the start of the oxidation reaction were, at a reaction temperature of 260° C., as follows: conversion of acrolein=99.1 mol %, selectivity of acrylic acid=95.1 mol %, yield of acrylic acid=94.2 mol%.

TABLE 1

| | | Compositional distribution in catalyst particle (inside of particle/outer surface of particle) | Maldistribution ratio (%) | |
|---|---|---|---|---|
| | Catalyst | | Surface-side maldistribution ratio (Ma) of W | Core-side maldistribution ratio (Mc) of Cu |
| Example 1-1 | Catalyst (1-1) | Dried material (A)/dried material (B) | 64 | 50 |
| Comparative Example 1-1 | Catalyst (c1-1) | Dried material (A) only | 50 | 50 |
| Comparative Example 1-2 | Catalyst (c1-2) | Dried material (B) only | 50 | 50 |
| Comparative Example 1-3 | Catalyst (c1-3) | Uniform mixture of dried materials (A) and (B) | 50 | 50 |
| Example 1-2 | Catalyst (1-2) | Dried material (A)/dried material (C) | 50 | 62 |
| Comparative Example 1-4 | Catalyst (c1-4) | Dried material (C) only | 50 | 50 |
| Referential Example 1-1 | Catalyst (r1-1) | Dried material (C)/dried material (A) | 47 | 43 |
| Example 1-3 | Catalyst (1-3) | Dried material (A)/dried material (D) | 65 | 60 |
| Example 1-4 | Catalyst (1-4) | Dried material (A)/dried material (E) | 65 | 59 |
| Example 1-5 | Catalyst (1-5) | Dried material (A)/dried material (F) | 63 | 62 |
| Example 1-6 | Catalyst (1-6) | Dried material (C)/dried material (E) | 64 | 50 |
| Example 1-7 | Catalyst (1-7) | Dried material (C)/dried material (F) | 62 | 52 |
| Example 1-8 | Catalyst (1-8) | Dried material (B)/dried material (E) | 50 | 58 |
| Example 1-9 | Catalyst (1-9) | Dried material (B)/dried material (F) | 50 | 60 |

TABLE 2

| | Catalyst | Compositional distribution in catalyst particle (inside of particle/outer surface of particle) | At passage of 100 hours from start of oxidation reaction | | At passage of 2,000 hours from start of oxidation reaction | |
|---|---|---|---|---|---|---|
| | | | Reaction temperature (° C.) | Selectivity of acrylic acid (mol %) | Reaction temperature (° C.) | Selectivity of acrylic acid (mol %) |
| Example 1-1 | Catalyst (1-1) | Dried material (A)/dried material (B) | 271 | 94.0 | 303 | 92.9 |
| Comparative Example 1-1 | Catalyst (c1-1) | Dried material (A) only | 275 | 93.7 | 321 | 91.3 |
| Comparative Example 1-2 | Catalyst (c1-2) | Dried material (B) only | 270 | 93.4 | 308 | 91.1 |
| Comparative Example 1-3 | Catalyst (c1-3) | Uniform mixture of dried materials (A) and (B) | 273 | 93.5 | 310 | 91.8 |
| Example 1-2 | Catalyst (1-2) | Dried material (A)/dried material (C) | 272 | 94.1 | 304 | 93.0 |
| Comparative Example 1-4 | Catalyst (c1-4) | Dried material (C) only | 268 | 93.4 | 305 | 91.3 |
| Referential Example 1-1 | Catalyst (r1-1) | Dried material (C)/dried material (A) | 275 | 94.8 | 319 | 92.3 |
| Example 1-3 | Catalyst (1-3) | Dried material (A)/dried material (D) | 269 | 94.0 | 295 | 93.2 |
| Example 1-4 | Catalyst (1-4) | Dried material (A)/dried material (E) | 272 | 94.5 | 301 | 93.4 |
| Example 1-5 | Catalyst (1-5) | Dried material (A)/dried material (F) | 266 | 93.8 | 290 | 93.2 |
| Example 1-6 | Catalyst (1-6) | Dried material (C)/dried material (E) | 271 | 94.5 | 302 | 93.3 |
| Example 1-7 | Catalyst (1-7) | Dried material (C)/dried material (F) | 266 | 94.0 | 291 | 93.0 |
| Example 1-8 | Catalyst (1-8) | Dried material (B)/dried material (E) | 270 | 94.3 | 299 | 93.1 |
| Example 1-9 | Catalyst (1-9) | Dried material (B)/dried material (F) | 266 | 93.8 | 290 | 92.8 |

[Second Catalyst]:

Example 2-1

(Production of Catalyst):

A silica-alumina support of 5.0 mm in average diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, first dried material (A) was added and thereby supported onto the support. Subsequently, the dried material (G) was added and thereby supported onto the outside of the dried material (A), thus obtaining a supported structure.

Next, this supported structure was taken out and then calcined at 400° C. under an air atmosphere for 6 hours, thus obtaining a spherical catalyst (2-1). Incidentally, as to the dried materials (A) and (G), their amounts of addition into the tumbling granulator were adjusted so that their respective supporting ratios would be 10 mass % after the calcination.

The resultant catalyst (2-1) was cut off into hemispheres along a plane passing through the center of the catalyst. A cut section of this hemispherical catalyst was analyzed with the EPMA device into vanadium linearly from a one-side outer surface through the central portion to the opposite-side outer surface in the above section. Based on the results of this analysis, as to the vanadium, the surface-side maldistribution ratio Ma (%) was determined from the aforementioned formula (a) with the standard position defined as $1/2r^1$. Its results are shown in Table 3.

(Oxidation Reaction):

A stainless reaction tube of 25 mm in inner diameter and 800 mm in length as heated with a molten nitrate was packed with 100 mL of the catalyst (2-1). Then, a mixed gas of acrolein 4 volume %, oxygen 4 volume %, water vapor 30 volume %, and nitrogen 62 volume % was introduced into the reaction tube at a space velocity of 2,500 $hr^{-1}$ (STP) to thus carry out an oxidation reaction of acrolein continuously. During this, the reaction temperature was adjusted so that the conversion of acrolein might be maintained in the range of 98 to 99 mol %. The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 4.

Comparative Example 2-1

(Production of Catalyst):

A silica-alumina support of 4.5 to 5.0 mm in diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, the dried material (A) was added and thereby supported onto the support. The resultant supported structure was taken out and then calcined at 400° C. under an air atmosphere for 6 hours, thus obtaining a spherical catalyst (c2-1). Incidentally, as to the dried material (A), its amount of addition into the tumbling granulator was adjusted so that its supporting ratio would be 20 mass % after the calcination.

As to the resultant catalyst (c2-1), the surface-side maldistribution ratio Ma (%) of the vanadium was determined in the same way as of Example 2-1. Its results are shown in Table 3.

(Oxidation Reaction):

An oxidation reaction was carried out in the same way as of Example 2-1 except that the catalyst (2-1) was replaced with the catalyst (c2-1). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 4.

Comparative Example 2-2

(Production of Catalyst):

A spherical catalyst (c2-2) was obtained in the same way as of the catalyst production process of Comparative Example 2-1 except that the dried material (A) was replaced with the dried material (G).

As to the resultant catalyst (c2-2), the surface-side maldistribution ratio Ma (%) of the vanadium was determined in the same way as of Example 2-1. Its results are shown in Table 3.

(Oxidation Reaction):

An oxidation reaction was carried out in the same way as of Example 2-1 except that the catalyst (2-1) was replaced with the catalyst (c2-2). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 4.

Comparative Example 2-3

(Production of Catalyst):

A spherical catalyst (c2-3) was obtained in the same way as of the catalyst production process of Comparative Example 2-1 except that the dried material (A) was replaced with a mixed powder having been obtained by uniformly mixing the dried materials (A) and (G) in equal quantities together. Incidentally, as to the dried materials (A) and (G), their amounts of addition into the tumbling granulator were adjusted so that their respective supporting ratios would be 10 mass % after the calcination.

As to the resultant catalyst (c2-3), the surface-side maldistribution ratio Ma (%) of the vanadium was determined in the same way as of Example 2-1. Its results are shown in Table 3.

(Oxidation Reaction):

An oxidation reaction was carried out in the same way as of Example 2-1 except that the catalyst (2-1) was replaced with the catalyst (c2-3). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 4.

Referential Example 2-1

(Production of Catalyst):

A spherical catalyst (r2-1) was obtained in the same way as of the catalyst production process of Example 2-1 except that the dried material (A) was replaced with the dried material (G), and that the dried material (G) was replaced with the dried material (A).

As to the resultant catalyst (r2-1), the surface-side maldistribution ratio Ma (%) of the vanadium was determined in the same way as of Example 2-1. Its results are shown in Table 3.

(Oxidation Reaction):

An oxidation reaction was carried out in the same way as of Example 2-1 except that the catalyst (2-1) was replaced with the catalyst (r2-1). The reaction temperature and the selectivity of acrylic acid at a passage of 100 hours from the start of the oxidation reaction, and the reaction temperature and the selectivity of acrylic acid at a passage of 2,000 hours from the start of the oxidation reaction, are shown in Table 4.

Example 2-2

(Oxidation Reaction):

A stainless reaction tube of 25 mm in inner diameter and 3,000 mm in length as heated with a molten nitrate was packed with 1,000 mL of the catalyst (2-1). Then, a mixed gas of acrolein 5 volume %, air 25 volume %, water vapor 30 volume %, and an inert gas (e.g. nitrogen) 40 volume % was introduced into the reaction tube at a space velocity of 1,600 hr$^{-1}$ (STP) to thus carry out an oxidation reaction. The results of the oxidation reaction at a passage of 100 hours from the start of the oxidation reaction were, at a reaction temperature of 262° C., as follows: conversion of acrolein=99.3 mol %, selectivity of acrylic acid 94.6 mol %, yield of acrylic acid=93.9 mol %.

TABLE 3

|  | Catalyst | Compositional distribution in catalyst particle (inside of particle/outer surface of particle) | Maldistribution ratio (%) Surface-side maldistribution ratio (Ma) of V |
|---|---|---|---|
| Example 2-1 | Catalyst (2-1) | Dried material (A)/dried material (G) | 54 |
| Comparative Example 2-1 | Catalyst (c2-1) | Dried material (A) only | 50 |
| Comparative Example 2-2 | Catalyst (c2-2) | Dried material (G) only | 50 |
| Comparative Example 2-3 | Catalyst (c2-3) | Uniform mixture of dried materials (A) and (G) | 50 |
| Referential Example 2-1 | Catalyst (r2-1) | Dried material (G)/dried material (A) | 45 |

TABLE 4

|  | Catalyst | Compositional distribution in catalyst particle (inside of particle/outer surface of particle) | At passage of 100 hours from start of oxidation reaction | | At passage of 2,000 hours from start of oxidation reaction | |
|---|---|---|---|---|---|---|
|  |  |  | Reaction temperature (° C.) | Selectivity of acrylic acid (mol %) | Reaction temperature (° C.) | Selectivity of acrylic acid (mol %) |
| Example 2-1 | Catalyst (2-1) | Dried material (A)/dried material (G) | 271 | 93.7 | 303 | 92.6 |
| Comparative Example 2-1 | Catalyst (c2-1) | Dried material (A) only | 275 | 93.7 | 321 | 91.3 |
| Comparative Example 2-2 | Catalyst (c2-2) | Dried material (G) only | 268 | 92.9 | 302 | 90.7 |
| Comparative Example 2-3 | Catalyst (c2-3) | Uniform mixture of dried materials (A) and (G) | 272 | 93.2 | 311 | 90.9 |
| Referential Example 2-1 | Catalyst (r2-1) | Dried material (G)/dried material (A) | 273 | 94.4 | 314 | 91.8 |

[Third Catalyst]:

Example 3-1

(Production of Catalyst):

A silica-alumina support of 5.0 mm in average diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, first the dried material (B) was added and thereby supported onto the support. Subsequently, the dried material (A) was added and thereby supported onto the outside of the dried material (B), thus obtaining a supported structure.

Next, this supported structure was taken out and then calcined at 400° C. under an air atmosphere for 6 hours, thus obtaining a spherical catalyst (3-1). Incidentally, as to the dried materials (A) and (B), their amounts of addition into the tumbling granulator were adjusted so that their respective supporting ratios would be 10 mass % after the calcination.

The resultant catalyst (3-1) was cut off into hemispheres along a plane passing through the center of the catalyst. A cut section of this hemispherical catalyst was analyzed with the EPMA device into copper and tungsten linearly from a one-side outer surface through the central portion to the opposite-side outer surface in the above section. Based on the results of this analysis, as to the copper, the surface-side maldistribution ratio Ma (%) was determined from the aforementioned formula (.alpha.) with the standard position defined as $1/2r^1$. Along therewith, as to the tungsten, the core-side maldistribution ratio Mc (%) was determined from the aforementioned formula (c) with the standard position defined as $1/2r^1$. The results are shown in Table 5.

(Oxidation Reaction):

A stainless reaction tube of 25 mm in inner diameter and 800 mm in length as heated with a molten nitrate was packed with 100 mL of the catalyst (3-1). Then, a mixed gas of acrolein 4 volume %, oxygen 4 volume %, water vapor 30 volume %, and nitrogen 62 volume % was introduced into the reaction tube at a space velocity of 2,500 $hr^{-1}$ (STP) to thus carry out an oxidation reaction of acrolein continuously. During this, the reaction temperature was adjusted so that the conversion of acrolein might be maintained in the range of 98 to 99 mol %. The reaction temperature and the selectivity of acrylic acid at a passage of 100 hours from the start of the oxidation reaction are shown in Table 6.

Comparative Example 3-1

(Production of Catalyst):

A silica-alumina support of 4.5 to 5.0 mm in diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, the dried material (A) was added and thereby supported onto the support. The resultant supported structure was taken out and then calcined at 400° C. under an air atmosphere for 6 hours, thus obtaining a spherical catalyst (c3-1). Incidentally, as to the dried material (A), its amount of addition into the tumbling granulator was adjusted so that its supporting ratio would be 20 mass % after the calcination.

As to the resultant catalyst (c3-1), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (c3-1). The reaction temperature and the selectivity of acrylic acid at a passage of 100 hours from the start of the oxidation reaction are shown in Table 6.

Comparative Example 3-2

(Production of Catalyst):

A spherical catalyst (c3-2) was obtained in the same way as of the catalyst production process of Comparative Example 3-1 except that the dried material (A) was replaced with the dried material (B).

As to the resultant catalyst (c3-2), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (c3-2). The reaction temperature and the selectivity of acrylic acid at a passage of 100 hours from the start of the oxidation reaction are shown in Table 6.

Comparative Example 3-3

(Production of Catalyst):

A spherical catalyst (c3-3) was obtained in the same way as of the catalyst production process of Comparative Example 3-1 except that the dried material (A) was replaced with a mixed powder having been obtained by uniformly mixing the dried materials (A) and (B) in equal quantities together. Incidentally, as to the dried materials (A) and (B), their amounts of addition into the tumbling granulator were adjusted so that their respective supporting ratios would be 10 mass % after the calcination.

As to the resultant catalyst (c3-3), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (c3-3). The reaction temperature and the selectivity of acrylic acid at a passage of 100 hours from the start of the oxidation reaction are shown in Table 6.

Example 3-2

(Production of Catalyst):

A spherical catalyst (3-2) was obtained in the same way as of the catalyst production process of Example 3-1 except that the dried material (B) was replaced with the dried material (C).

As to the resultant catalyst (c3-2), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (3-2). The reaction temperature and the selectivity of acrylic acid at a passage of 100 hours from the start of the oxidation reaction are shown in Table 6.

Comparative Example 3-4

(Production of Catalyst):

A spherical catalyst (c3-4) was obtained in the same way as of the catalyst production process of Comparative Example 3-1 except that the dried material (A) was replaced with the dried material (C).

As to the resultant catalyst (c3-4), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (c3-4). The reaction temperature and the selectivity of acrylic acid at a passage of 100 hours from the start of the oxidation reaction are shown in Table 6.

Referential Example 3-1

(Production of Catalyst):

A spherical catalyst (r3-1) was obtained in the same way as of the catalyst production process of Example 3-1 except that the dried material (B) was replaced with the dried material (A), and that the dried material (A) was replaced with the dried material (C).

As to the resultant catalyst (r3-1), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (r3-1). The reaction temperature and the selectivity of acrylic acid at a passage of 100 hours from the start of the oxidation reaction are shown in Table 6.

Referential Example 3-2

(Production of Catalyst):

A spherical catalyst (r3-2) was obtained in the same way as of the catalyst production process of Example 3-1 except that the dried material (B) was replaced with the dried material (C), and that the dried material (A) was replaced with the dried material (F).

As to the resultant catalyst (r3-2), the surface-side maldistribution ratio Ma (%) of the copper and the core-side maldistribution ratio Mc (%) of the tungsten were determined in the same way as of Example 3-1. The results are shown in Table 5.

(Oxidation Reaction):

An oxidation reaction was carried out in the same way as of Example 3-1 except that the catalyst (3-1) was replaced with the catalyst (r3-2). The reaction temperature and selectivity of acrylic acid at a passage of 100 hours from the start of the oxidation reaction are shown in Table 6.

Examples 3-3 and 3-4

(Production of Catalysts):

Spherical catalysts (3-3) and (3-4) were obtained in the same way as of the catalyst production process of Example 3-1 except that the dried material (B) was replaced with the dried materials (E) and (F) respectively.

As to the resultant catalysts (3-3) and (3-4), the surface-side maldistribution ratio Ma (%) of the copper and the core-side maldistribution ratio Mc (%) of the tungsten were determined in the same way as of Example 3-1. The results are shown in Table 5.

(Oxidation Reactions):

Oxidation reactions were carried out in the same way as of Example 3-1 except that the catalyst (3-1) was replaced with the catalysts (3-3) and (3-4) respectively. The reaction temperature and the selectivity of acrylic acid at a passage of 100 hours from the start of each oxidation reaction are shown in Table 6.

Examples 3-5 to 3-8

(Production of Catalysts):

Spherical catalysts (3-5), (3-6), (3-7), and (3-8) were obtained in the same way as of the catalyst production process of Example 3-1 except that the dried material (B) was replaced with either of the dried materials (E) and (F) respectively, and that the dried material (A) was replaced with either of the dried materials (B) and (C) respectively (for the specific combinations of the dried materials used, refer to Tables 5 and 6).

As to the resultant catalysts (3-5), (3-6), (3-7), and (3-8), the surface-side maldistribution ratio Ma (%) of the copper and the core-side maldistribution ratio Mc (%) of the tungsten were determined in the same way as of Example 3-1. The results are shown in Table 5.

(Oxidation Reactions):

Oxidation reactions were carried out in the same way as of Example 3-1 except that the catalyst (3-1) was replaced with the catalysts (3-5), (3-6), (3-7), and (3-8) respectively. The reaction temperature and the selectivity of acrylic acid at a passage of 100 hours from the start of each oxidation reaction are shown in Table 6.

Example 3-9

(Oxidation Reaction):

A stainless reaction tube of 25 mm in inner diameter and 3,000 mm in length as heated with a molten nitrate was packed with 1,000 mL of the catalyst (3-2). Then, a mixed gas of acrolein 5 volume %, air 25 volume %, water vapor 30 volume %, and an inert gas (e.g. nitrogen) 40 volume % was introduced into the reaction tube at a space velocity of 1,600 hr$^{-1}$ (STP) to thus carry out an oxidation reaction. The results of the oxidation reaction at a passage of 100 hours from the start of the oxidation reaction were, at a reaction temperature of 264° C., as follows: conversion of acrolein=99.0 mol %, selectivity of acrylic acid=95.9 mol %, yield of acrylic acid=94.9 mol %.

TABLE 5

| | Catalyst | Compositional distribution in catalyst particle (inside of particle/outer surface of particle) | Maldistribution ratio (%) | |
|---|---|---|---|---|
| | | | Surface-side maldistribution ratio (Ma) of Cu | Core-side maldistribution ratio (Mc) of W |
| Example 3-1 | Catalyst (3-1) | Dried material (B)/dried material (A) | 50 | 64 |
| Comparative Example 3-1 | Catalyst (c3-1) | Dried material (A) only | 50 | 50 |
| Comparative Example 3-2 | Catalyst (c3-2) | Dried material (B) only | 50 | 50 |
| Comparative Example 3-3 | Catalyst (c3-3) | Uniform mixture of dried materials (A) and (B) | 50 | 50 |
| Example 3-2 | Catalyst (3-2) | Dried material (C)/dried material (A) | 60 | 50 |
| Comparative Example 3-4 | Catalyst (c3-4) | Dried material (C) only | 50 | 50 |
| Referential Example 3-1 | Catalyst (r3-1) | Dried material (A)/dried material (C) | 42 | 50 |
| Referential Example 3-2 | Catalyst (r3-2) | Dried material (C)/dried material (F) | 50 | 40 |
| Example 3-3 | Catalyst (3-3) | Dried material (E)/dried material (A) | 58 | 66 |
| Example 3-4 | Catalyst (3-4) | Dried material (F)/dried material (A) | 60 | 64 |
| Example 3-5 | Catalyst (3-5) | Dried material (E)/dried material (C) | 50 | 65 |
| Example 3-6 | Catalyst (3-6) | Dried material (F)/dried material (C) | 50 | 64 |
| Example 3-7 | Catalyst (3-7) | Dried material (E)/dried material (B) | 58 | 50 |
| Example 3-8 | Catalyst (3-8) | Dried material (F)/dried material (B) | 60 | 50 |

TABLE 6

| | Catalyst | Compositional distribution in catalyst particle (inside of particle/outer surface of particle) | At passage of 100 hours from start of oxidation reaction | |
|---|---|---|---|---|
| | | | Reaction temperature (° C.) | Selectivity of acrylic acid (mol %) |
| Example 3-1 | Catalyst (3-1) | Dried material (B)/dried material (A) | 274 | 94.8 |
| Comparative Example 3-1 | Catalyst (c3-1) | Dried material (A) only | 275 | 93.7 |
| Comparative Example 3-2 | Catalyst (c3-2) | Dried material (B) only | 270 | 93.4 |
| Comparative Example 3-3 | Catalyst (c3-3) | Uniform mixture of dried materials (A) and (B) | 273 | 93.5 |
| Example 3-2 | Catalyst (3-2) | Dried material (C)/dried material (A) | 275 | 94.8 |
| Comparative Example 3-4 | Catalyst (c3-4) | Dried material (C) only | 268 | 93.4 |
| Referential Example 3-1 | Catalyst (r3-1) | Dried material (A)/dried material (C) | 272 | 94.1 |
| Referential Example 3-2 | Catalyst (r3-2) | Dried material (C)/dried material (F) | 266 | 94.0 |
| Example 3-3 | Catalyst (3-3) | Dried material (E)/dried material (A) | 273 | 95.2 |
| Example 3-4 | Catalyst (3-4) | Dried material (F)/dried material (A) | 270 | 94.7 |
| Example 3-5 | Catalyst (3-5) | Dried material (E)/dried material (C) | 274 | 95.2 |
| Example 3-6 | Catalyst (3-6) | Dried material (F)/dried material (C) | 271 | 94.9 |
| Example 3-7 | Catalyst (3-7) | Dried material (E)/dried material (B) | 273 | 95.1 |
| Example 3-8 | Catalyst (3-8) | Dried material (F)/dried material (B) | 272 | 94.8 |

[Fourth Catalyst]:

Example 4-1

(Production of Catalyst):

A silica-alumina support of 5.0 mm in average diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, first the dried material (G) was added and thereby supported onto the support. Subsequently, the dried material (A) was added and thereby supported onto the outside of the dried material (G), thus obtaining a supported structure.

Next, this supported structure was taken out and then calcined at 400° C. under an air atmosphere for 6 hours, thus obtaining a spherical catalyst (4-1). Incidentally, as to the dried materials (A) and (G), their amounts of addition into the tumbling granulator were adjusted so that their respective supporting ratios would be 10 mass % after the calcination.

The resultant catalyst (4-1) was cut off into hemispheres along a plane passing through the center of the catalyst. A cut section of this hemispherical catalyst was analyzed with the EPMA device into vanadium linearly from a one-side outer surface through the central portion to the opposite-side outer surface in the above section. Based on the results of this analysis, as to the vanadium, the core-side maldistribution ratio Mc (%) was determined from the aforementioned formula (c) with the standard position defined as $1/2r^1$. Its results are shown in Table 7.

(Oxidation Reaction):

A stainless reaction tube of 25 mm in inner diameter and 800 mm in length as heated with a molten nitrate was packed with 100 mL of the catalyst (4-1). Then, a mixed gas of acrolein 4 volume %, oxygen 4 volume %, water vapor 30 volume %, and nitrogen 62 volume % was introduced into the reaction tube at a space velocity of 2,500 $hr^{-1}$ (STP) to thus carry out an oxidation reaction of acrolein continuously. During this, the reaction temperature was adjusted so that the conversion of acrolein might be maintained in the range of 98 to 99 mol %. The reaction temperature and the selectivity of acrylic acid at a passage of 100 hours from the start of the oxidation reaction are shown in Table 8.

Comparative Example 4-1

(Production of Catalyst):

A silica-alumina support of 4.5 to 5.0 mm in diameter was put into a rotary dish of a dish type tumbling granulator. While the rotary dish was rotated at a revolution rate of 15 rpm in a state tilted at 30° to the horizontal plane, a 10 mass % aqueous ethylene glycol solution was sprayed to the support. After this spraying had been carried out for 10 minutes, the dried material (A) was added and thereby supported onto the support. The resultant supported structure was taken out and then calcined at 400° C. under an air atmosphere for 6 hours, thus obtaining a spherical catalyst (c4-1). Incidentally, as to the dried material (A), its amount of addition into the tumbling granulator was adjusted so that its supporting ratio would be 20 mass % after the calcination.

As to the resultant catalyst (c4-1), the core-side maldistribution ratio Mc (%) of the vanadium was determined in the same way as of Example 4-1. Its results are shown in Table 7.

(Oxidation Reaction):

An oxidation reaction was carried out in the same way as of Example 4-1 except that the catalyst (4-1) was replaced with the catalyst (c4-1). The reaction temperature and the selectivity of acrylic acid at a passage of 100 hours from the start of the oxidation reaction are shown in Table 8.

Comparative Example 4-2

(Production of Catalyst):

A spherical catalyst (c4-2) was obtained in the same way as of the catalyst production process of Comparative Example 4-1 except that the dried material (A) was replaced with the dried material (G).

As to the resultant catalyst (c4-2), the core-side maldistribution ratio Mc (%) of the vanadium was determined in the same way as of Example 4-1. Its results are shown in Table 7.

(Oxidation Reaction):

An oxidation reaction was carried out in the same way as of Example 4-1 except that the catalyst (4-1) was replaced with the catalyst (c4-2). The reaction temperature and the selectivity of acrylic acid at a passage of 100 hours from the start of the oxidation reaction are shown in Table 8.

Comparative Example 4-3

(Production of Catalyst):

A spherical catalyst (c4-3) was obtained in the same way as of the catalyst production process of Comparative Example 4-1 except that the dried material (A) was replaced with a mixed powder having been obtained by uniformly mixing the dried materials (A) and (G) in equal quantities together. Incidentally, as to the dried materials (A) and (G), their amounts of addition into the tumbling granulator were adjusted so that their respective supporting ratios would be 10 mass % after the calcination.

As to the resultant catalyst (c4-3), the core-side maldistribution ratio Mc (%) of the vanadium was determined in the same way as of Example 4-1. Its results are shown in Table 7.

(Oxidation Reaction):

An oxidation reaction was carried out in the same way as of Example 4-1 except that the catalyst (4-1) was replaced with the catalyst (c4-3). The reaction temperature and the selectivity of acrylic acid at a passage of 100 hours from the start of the oxidation reaction are shown in Table 8.

Referential Example 4-1

(Production of Catalyst):

A spherical catalyst (r4-1) was obtained in the same way as of the catalyst production process of Example 4-1 except that the dried material (G) was replaced with the dried material (A), and that the dried material (A) was replaced with the dried material (G).

As to the resultant catalyst (r4-1), the core-side maldistribution ratio Mc (%) of the vanadium was determined in the same way as of Example 4-1. Its results are shown in Table 7.

(Oxidation Reaction):

An oxidation reaction was carried out in the same way as of Example 4-1 except that the catalyst (4-1) was replaced with the catalyst (r4-1). The reaction temperature and the selectivity of acrylic acid at a passage of 100 hours from the start of the oxidation reaction are shown in Table 8.

Example 4-2

(Oxidation Reaction):

A stainless reaction tube of 25 mm in inner diameter and 3,000 mm in length as heated with a molten nitrate was packed with 1,000 mL of the catalyst (4-1). Then, a mixed gas of acrolein 5 volume %, air 25 volume %, water vapor 30 volume %, and an inert gas (e.g. nitrogen) 40 volume % was introduced into the reaction tube at a space velocity of 1,600 $hr^{-1}$ (STP) to thus carry out an oxidation reaction. The results of the oxidation reaction at a passage of 100 hours from the start of the oxidation reaction were, at a reaction temperature of 263° C., as follows: conversion of acrolein=98.8 mol %, selectivity of acrylic acid=96.0 mol %, yield of acrylic acid=94.8 mol %.

TABLE 7

| | Catalyst | Compositional distribution in catalyst particle (inside of particle/outer surface of particle) | Maldistribution ratio (%) Surface-side maldistribution ratio (Ma) of V |
|---|---|---|---|
| Example 4-1 | Catalyst (4-1) | Dried material (G)/dried material (A) | 55 |
| Comparative Example 4-1 | Catalyst (c4-1) | Dried material (A) only | 50 |
| Comparative Example 4-2 | Catalyst (c4-2) | Dried material (G) only | 50 |
| Comparative Example 4-3 | Catalyst (c4-3) | Uniform mixture of dried materials (A) and (G) | 50 |
| Referential Example 4-1 | Catalyst (r4-1) | Dried material (A)/dried material (G) | 46 |

TABLE 8

| | Catalyst | Compositional distribution in catalyst particle (inside of particle/outer surface of particle) | At passage of 100 hours from start of oxidation reaction | |
|---|---|---|---|---|
| | | | Reaction temperature (° C.) | Selectivity of acrylic acid (mol %) |
| Example 4-1 | Catalyst (4-1) | Dried material (G)/dried material (A) | 273 | 94.4 |
| Comparative Example 4-1 | Catalyst (c4-1) | Dried material (A) only | 275 | 93.7 |
| Comparative Example 4-2 | Catalyst (c4-2) | Dried material (G) only | 268 | 92.9 |
| Comparative Example 4-3 | Catalyst (c4-3) | Uniform mixture of dried materials (A) and (G) | 272 | 93.2 |
| Referential Example 4-1 | Catalyst (r4-1) | Dried material (A)/dried material (G) | 271 | 93.7 |

INDUSTRIAL APPLICATION

The catalyst according to the present invention is favorable as a catalyst for production of acrylic acid.

The production process according to the present invention is favorable for production of acrylic acid.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A fixed-bed reactor catalyst for preparing acrylic acid, wherein the fixed-bed reactor catalyst is an eggshell type catalyst comprising:
   a) a support and a catalytic component supported on an outer support surface of the support;
   b) wherein said catalytic component includes a support surface side, an outer surface side, and a catalytic outer surface, wherein said catalytic outer surface is on said outer surface side;
   c) wherein said catalytic component comprises an oxide represented by the formula (1):

$$Mo_aV_bW_cCu_dO_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1\leq b\leq 14$, $0\leq c\leq 12$, $0\leq d\leq 10$, and $0<c+d$; and x is a numerical value determined by oxidation states of the elements);
   d) wherein: the tungsten is maldistributed in the outer surface side of the catalytic component; and/or the copper is maldistributed in the support surface side of the catalytic component;
   e) wherein in the case of tungsten: an outer surface side maidistribution ratio (Ma (%)) of said tungsten is more than 50% such that more than 50% of a total content of tungsten is found from a middle of the catalytic component to said catalytic outer surface; and
   f) wherein in the case of copper: a support surface side maldistribution ratio (Mc (%)) of said copper is more than 50% such that more than 50% of a total content of copper is found from a middle of the catalytic component to said support surface of the support.

2. A fixed-bed reactor catalyst for preparing acrylic acid, wherein the fixed-bed reactor catalyst is an eggshell type catalyst comprising:
   a) a support and a catalytic component supported on an outer support surface of the support;
   b) wherein said catalytic component includes a support surface side, an outer surface side, and a catalytic outer surface, wherein said catalytic outer surface is on said outer surface side;
   c) wherein said catalytic component comprises an oxide represented by the formula (1):

$$Mo_aV_bW_cCu_dO_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1\leq b\leq 14$, $0\leq c\leq 12$, $0\leq d\leq 10$, and $0<c+d$; and x is a numerical value determined by oxidation states of the elements);
   d) wherein: the vanadium is maldistributed in the outer surface side of the catalytic component; and
   e) wherein in the case of vanadium: an outer surface side maldistribution ratio (Ma (%)) of said vanadium is more than 50% such that more than 50% of a total content of vanadium is found from a middle of the catalytic component to said catalytic outer surface.

3. A fixed-bed reactor catalyst for preparing acrylic acid, wherein the fixed-bed reactor catalyst is an eggshell type catalyst comprising:
   a) a support and a catalytic component supported on an outer support surface of the support;
   b) wherein said catalytic component includes a support surface side, an outer surface side, and a catalytic outer surface, wherein said catalytic outer surface is on said outer surface side;
   c) wherein said catalytic component comprises an oxide represented by the formula (1):

$$Mo_aV_bW_cCu_dO_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1\leq b\leq 14$, $0\leq c\leq 12$, $0\leq d\leq 10$, and $0<c+d$; and x is a numerical value determined by oxidation states of the elements);
   d) wherein: the copper is maldistributed in the outer surface side of the catalytic component; and/or the tungsten is maldistributed in the support surface side of the catalytic component;
   e) wherein in the case of copper: an cuter surface side maldistribution ratio (Ma (%)) of said copper is more than 50% such that more than 50% of a total content of copper is found from a middle of the catalytic component to said catalytic outer surface;
   f) wherein in the case of tungsten: a support surface side maldistribution ratio (Mc (%)) of said tungsten is more than 50% such that more than 50% of a total content of tungsten is found from a middle of the catalytic component to said support surface of the support.

4. A fixed-bed reactor catalyst for preparing acrylic acid, wherein the fixed-bed reactor catalyst is an eggshell type catalyst comprising:
   a) a support and a catalytic component supported on an outer support surface of the support;
   b) wherein said catalytic component includes a support surface side, an outer surface side, and a catalytic outer surface, wherein said catalytic outer surface is on said outer surface side;
   c) wherein said catalytic component comprises an oxide represented by the formula (1):

$$Mo_a V_b W_c Cu_d O_x \quad (1)$$

(wherein: Mo is molybdenum; V is vanadium; W is tungsten; Cu is copper; and O is oxygen; and a, b, c, d, and x denote atomic ratios of Mo, V, W, Cu, and O respectively; when a=12, then $1 \leq b \leq 14$, $0 \leq c \leq 12$, $0 \leq d \leq 10$, and $0<c+d$; and x is a numerical value determined by oxidation states of the elements);
   d) wherein the vanadium is maldistributed in the support surface side of the catalytic component; and
   e) wherein in the case of vanadium: a support surface side maldistribution ratio (Mc (%)) of said vanadium is more than 50% such that more than 50% of a total content of vanadium is found from a middle of the catalytic component to said support surface of the support.

5. A process for preparing acrylic acid, comprising the step of carrying out catalytic gas phase oxidation of acrolein in the presence of the fixed-bed reactor catalyst according to any one of claims 1, 2, 3 and 4 and molecular oxygen.

6. The fixed-bed reactor catalyst for preparing acrylic acid according to claim 1, wherein the outer surface side maldistribution ratio (Ma (%)) of said tungsten is not less than 55%.

7. The fixed-bed reactor catalyst for preparing acrylic acid according to claim 1, wherein the outer surface side maldistribution ratio (Ma (%)) of said tungsten is not less than 60%.

8. The fixed-bed reactor catalyst for preparing acrylic acid according to claim 1, wherein the support surface side maldistribution ratio (Mc (%)) of said copper is not less than 55%.

9. The fixed-bed reactor catalyst for preparing acrylic acid according to claim 1, wherein the support surface side maldistribution ratio (Mc (%)) of said copper is not less than 60%.

10. The fixed-bed reactor catalyst for preparing acrylic acid according to claim 2, wherein the outer surface side maldistribution ratio (Ma (%)) of said vanadium is not less than 55%.

11. The fixed-bed reactor catalyst for preparing acrylic acid according to claim 2, wherein the outer surface side maldistribution ratio (Ma (%)) of said vanadium is not less than 60%.

12. The fixed-bed reactor catalyst for preparing acrylic acid according to claim 3, wherein the outer surface side maldistribution ratio (Ma (%)) of said copper is not less than 55%.

13. The fixed-bed reactor catalyst for preparing acrylic acid according to claim 3, wherein the outer surface side maldistribution ratio (Ma (%)) of said copper is not less than 60%.

14. The fixed-bed reactor catalyst for preparing acrylic acid according to claim 3, wherein the support surface side maldistribution ratio (Mc (%)) of said tungsten is not less than 55%.

15. The fixed-bed reactor catalyst for preparing acrylic acid according to claim 3, wherein the support surface side maldistribution ratio (Mc (%)) of said tungsten is not less than 60%.

16. The fixed-bed reactor catalyst for preparing acrylic acid according to claim 4, wherein the support surface side maldistribution ratio (Mc (%)) of said vanadium is not less than 55%.

17. The fixed-bed reactor catalyst for preparing acrylic acid according to claim 4, wherein the support surface side maldistribution ratio (Mc (%)) of said vanadium is not less than 60%.

18. The fixed-bed reactor catalyst for preparing acrylic acid according to any one of claims 1, 2, 3 and 4, wherein the thickness of the catalytic component supported on the outer support surface of the support is not less than 30 μm.

19. The fixed-bed reactor catalyst for preparing acrylic acid according to any one of claims 1, 2, 3 and 4, wherein said catalytic component is supported on the outer support surface of the support and not inside of the support.

* * * * *